(12) United States Patent
Albini et al.

(10) Patent No.: US 6,444,639 B2
(45) Date of Patent: *Sep. 3, 2002

(54) HCG AND DERIVATIVES AS MATRIX METALLOPROTEASES INHIBITORS

(75) Inventors: Adriana Albini; Giorgia Orengo, both of Geneva (IT)

(73) Assignee: Applied Research Systems ARS Holding N.V., Curacao (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 14 days.

(21) Appl. No.: 09/242,099

(22) PCT Filed: Jul. 25, 1997

(86) PCT No.: PCT/EP97/04053

§ 371 (c)(1),
(2), (4) Date: Nov. 24, 1999

(87) PCT Pub. No.: WO98/05353

PCT Pub. Date: Feb. 12, 1998

(30) Foreign Application Priority Data

Aug. 7, 1996 (IT) ........................................ RM96A0566

(51) Int. Cl.$^7$ ........................ A61K 38/00; A61K 38/24; C07K 14/59
(52) U.S. Cl. ................................ 514/2; 514/8; 530/397; 530/398
(58) Field of Search .............................. 514/2, 8, 2.14; 530/397, 398, 323; 424/185.1

(56) References Cited

U.S. PATENT DOCUMENTS 5,968,513 A * 10/1999 Gallo et al. ............... 424/185.1

FOREIGN PATENT DOCUMENTS

| WO | 93/11788 | | 6/1993 |
| WO | WO 96/04008 | * | 2/1996 |
| WO | 97/14428 | | 4/1997 |

OTHER PUBLICATIONS

Lunardi–Iskandar et al. Tumorigenesis and metastasis of neoplastic Kaposi's sarcoma cell line in immunodeficient mice blocked by a human pregnancy hormone. Nature, vol. 375, pp. 64–68, Apr. 1995.*

Abstract—XP 002045882—Stamouli et al., "Suppressionof Matrix Metalloproteinase Production By hCG In Cultures Of Human Luteinized Granulosa Cells As A Model For Gonadotrophin–Induced Luteal Rescue", Journal of Reproduction and Fertility, 107(2)235–9 (Jul. 1996) Medline.

Abstract—XP 002045883—Yagel et al., "High Levels Of Human Chorionic Gonadotropin Retard First Trimester Trophoblast Ivasion In Vitro By Decreasing Urokinase Plasminogen Activator And Collagenase Activities", Journal of Clinical Endocrinology and Metabolism, 77(6)1506–11 (Dec. 1993) Medline.

Abstract—XP 002045884—Milwidsky et al., "Gonadotropin–Mediated Inhibition Of Proteolytic Enzymes Produced By Human Trophoblast In Culture", Journal of Clinical Endocrinology and Metabolism, 76(5)1101–5 (May 1993) Medline.

XP 002045881—Anderson et al., "Combination Therapy Including A Gelatinase Inhibitor And Cytotoxic Agent Reduces Local Invasion And Metastasis Of Murine Lewis Lung Carcinoma", Cancer Research, 715–718 (Feb. 1996).

XP 002023438—Sunardi–Iskandar et al., "Kaposi's Sarcoma In Pregnant Women", Nature, 377:21–22 (Sep. 1995).

Stamouli et al., "Suppression Of Matrix Metalloproteinase Production By hCG In Cultures Of Human Luteinized Granulosa Cells As A Model For Gonadotrophin–Induced Luteal Rescue", Journal of Reproduction and Fertility, 107:235–239 (1996).

Albini et al., "Angiogenic Potential In Vivo By Kaposi's Sarcoma Cell–Free Supernatants And HIV–1 Tat Product: Inhibition Of KS–Like Lesions By Tissue Inhibitor Of Metalloproteinase–2", AIDS, 8:1237–1244 (1994).

Albini et al., "Inhibition Of Invasion, Gelatinase Activity, Tumor Take And Metastasis Of Malignant Cells By N–Acetylcysteine", Int. J. Cancer, 61:121–129 (1995).

Anderson et al., "Stromelysin–3 Is Overexpressed By Stromal Elements In Primary Non–Small Cell Lung Cancers And Regulated By Retinoic Acid In Pulmonary Fibroblasts", Cancer Research, 55:4120–4126 (Sep. 1995).

Anderson et al., "Combination Therapy Including A Gelatinase Inhibitor And Cytotoxic Agent Reduces Local Invasion And Metastasis Of Murine Lewis Lung Carcinoma", Cancer Research, 56:715–718 (1996).

Benelli et al., "Inhibition Of Aids–Kaposi's Sarcoma Cell Induced Endothelial Cell Invasion By Timp–2 And A Synthetic Peptide From The Metalloproteinase Propetide: Implications For An Anti–Angiogenic Therapy", Oncology Research, 6:251–257 (1994).

(List continued on next page.)

Primary Examiner—Elizabeth Kemmerer
Assistant Examiner—Regina M. DeBerry
(74) Attorney, Agent, or Firm—Browdy and Neimark (57) ABSTRACT

The use of hCG, hCG β-subunit, as well as fragments and active derivatives thereof, or hCG β-core in the preparation of a medicament for the prophylaxis and/or the treatment of pathologies requiring inhibition of the matrix metalloprotease (MMP) enzymatic activity.

4 Claims, 8 Drawing Sheets

OTHER PUBLICATIONS

Bonassar et al., "In Vivo Effects Of Stroelysin On The Composition And Physical Properties Of Rabbit Articular Cartilage In The Presence And Absence Of A Synthetic Inhibitor", Arthritis & Rheumatism, 38:1678–1686 (Nov. 1995).

Boukamp et al., "Functional Evidence For Tumor Suppressor Activity On Chromosome 15 In Human Skin Carcinoma Cells And Thrombospondin–1 As The Potential Suppressor", German Cancer Research Center.

O'Byrne et al., "Oral Administration Of A Matrix Metalloproteinase Inhibitor, CGS 27023A, Protects The Cartilage Proteoglycan Matrix In A Partial Meniscectomy Model Of Osteoarthritis In Rabbits", Inflamm Res, 44:S117–S118 (1995).

Conway et al., "Inhibition Of Cartilage And Bone Destruction In Adjuvant Arthritis In The Rat By A Matrix Metalloproteinase Inhibitor", J. Exp. Med., 182:449–457 (Aug. 1995).

Dodwell et al., "The Potential For Proteinase Inhibitionin Cancer Treatment", Cancer Treatment Reviews, 19:283–296 (1993).

Galardy et al., "Inhibitionof Angiogenesis By The Matrix Metalloprotease Inhibitor N–[2R–2(Hydroxamidocarbonymethyl)4–Methylpentanoyl)]L–Tryptophan Methylamide", Cancer Research, 54:4715–4718 (Sep. 1994).

Gill et al., "The Effects Of Preparations Of Human Chorionic Gonadotropin On Aids–Related Kaposi's Sarcoma", Massachusetts Medical Society, 335:1261–1269 (1996).

Heussen et al., "Electrophoretic Analysis Of Plasminogen Activators In Polyacrylamide Gels Containing Sodium Dodecyl Sulfate And Copolymerized Substrates", Analytical Biochemistry, 102:196–202 (1980).

Kalyan et al., "Role of Carbohydrate In Human Chorionic Gonadotropin: Effect Of Deglycosylation On The Subunit Interaction And On Its In Vitro And In Vivo Biological Properties", The Journal of Biological Chemistry, 258:67–74 (1983).

Kleinman et al., "Basement Membran Complexes With Biological Activity", Biochemistry, 25:312–318 (1986).

Kohn et al., "Molecular Insights Into Cancer Invasion: Strategies For Prevention And Intervention", Cancer Research, 55:1856–1862 (May 1995).

Balakrishna et al., "Secretion Of Matrix Metalloproteinases And Their Inhibitors (Tissue Inhibitor Of Metalloproteinases) By Human Prostate In Explant Cultures: Reduced Tissue Inhibitor Of Metalloproteinase Secretion By Malignant Tissues", Cancer Research, 53:4493–4498 (Oct. 1993).

Melchiori et al., "Inhibition Of Tumor Cell Invasion By A Highly Conserved Peptide Sequence From The Matrix Metalloproteinase Enzyme Prosegment", Cancer Research, 52:2353–2356 (Apr. 1992).

Miltenburg et al., "Immobilized Anti–CD3 Antibody Activates T Cell Clones To Induce The Production Of Interstitial Collagenase, But Not Tissue Inhibitor Of Metall Oproteinases, In Monocytic THP–1 Cells And Dermal Fibroblasts", The American Association of Imunologists, 2655–2667 (1995).

Moses, "A Cartilage–Derived Inhibitor Of Neovascularization And Metalloproteinases", Clinical and Experimental Rheumatology, 11:S67–S69 (1993).

Powell et al., "Expression Of The Metalloproteinase Matrilysin In Du–145 Cells Increases Their Invasive Potential In Severe Combined Immunodeficient Mice", Cancer Research, 53:417–422 (Jan. 1993).

Ray et al., "Gelatinase A Activity Directly Modulates Melanoma Cell Adhsion And Speading", The EMBO Journal, 14:908–917 (1995).

Rosenberg et al., "Effect Of Steroids On CSF Matrix Metalloproteinases In Multiple Sclerosis: Relation To Blood–Brian Barrier Injury", American Academy of Neurology, 1626–1632 (Jun. 1996).

Siegal et al., "Development Of A Novel Human Extracellular Matrix For Quantitation Of The Invasiveness Of Human Cells", Cancer Letters, 69:123–132 (1993).

Stetler–Stevenson et al., "The Activation Of Human Type IV Collagenase Proenzyme: Sequence Identification Of The Major Conversion Product Following Organomercurial Activation", The Journal of Biological Chemistry, 264:1353–1356 (1989).

Vernon et al., "Between Molecules And Morphology Extracellular Matrix And Creation Of Vascular Form", American Journal of Pathology, 147:873–883 (Oct. 1995).

Wang et al., "Matrix Metalloproteinase Inhibitor BB–94 (Batimastat) Inhibits Human Colon Tumor Growth And Spread In A Patient–Like Orthotopic Model In Nude Mice", Cancer Research, 54:4726–4728, (Sep. 1994).

Woessner, "Matrix Metalloproteinases And Their Inhibitors In Connective Tissue Remodeling", The FASEB Journal, 5:2145–2154 (May 1991).

* cited by examiner

Inhibition of the gelatinolytic activity of KS-IMM cells by hCG

Zymographic analysis of type I collagenase

FIG. 3a

EXPERIMENTAL GROWTH OF KS IMM IN VIVO (CONTROLS)

FIG. 3b

EXPERIMENTAL GROWTH OF KS IMM IN VIVO (BETA-CORE 1 ug/MOUSE)

GROWTH OF KS IMM CELLS IN VIVO WITH r-hCG AND BETA-CORE TREATMENT

FIG. 6a

EXPERIMENTAL GROWTH OF KS IMM IN VIVO (CONTROLS) (13th DAY)

FIG. 6b

EXPERIMENTAL GROWTH OF KS IMM IN VIVO
(r-hCG 16 μg/MOUSE) (13th DAY)

FIG. 6c

EXPERIMENTAL GROWTH OF KS IMM IN VIVO
(BETA-CORE 5 μg/MOUSE) (13th DAY)

Inhibition of the gelatinolytic activity of KS-IMM cells and other cell lines by hCG

HCG AND DERIVATIVES AS MATRIX METALLOPROTEASES INHIBITORS

CROSS-REFERENCE TO RELATED APPLICATIONS

This application is a 371 national stage application of international PCT application PCT/EP97/04053, filed Jul. 25, 1997.

FIELD OF THE INVENTION

The present invention relates to the use of hCG, hCG β-subunit, as well as fragments and active derivatives thereof, or hCG β-core in the preparation of a medicament for the prophylaxis and/or the treatment of pathologies requiring inhibition of the matrix metalloprotease (MMP) enzymatic activity.

BACKGROUND OF THE INVENTION

Several pathological processes involve tissue remodeling and degradation, including tumor invasion, joint destruction in rheumatoid arthritis and osteoarthritis, periodontotitis and angiogenesis-dependent diseases such as corneal neovascularization, diabetic retinopathy, neovascular glaucoma, hemangioma, psoriasis, scleroderma and solid tumors.

Tumor invasion is a complex multistage process involving: a) tumor cell exit from the primary tumor and transit across host basement membrane; b) penetration (intravasation) and transit through the vascular system; c) arrest at distal site in the vasculature and exit from the circulation by repenetration of endothelial basement membrane (extravasation); d) entry into target tissue and proliferation at the secondary site.

One of the key events necessary to allow the passage of tumor cells is the removal of the extracellular matrix (ECM) by ECM degrading enzymes secreted by metastatic tumor cells and/or tumor-activated host stroma cells (D. J. Dodwell et al., 1993).

Basement membrane and interstitial connective tissue make up the ECM, which is composed by collagen, proteoglycans and adhesion glycoproteins. ECM provides a physical support to cells and tissues and cell-ECM interactions regulate cell growth, differentiation and migration.

ECM degrading enzymes include matrix metalloproteases (MMPs), urokinase, tissue plasminogen activator, cathepsins, trypsins and heparanases.

MMPs, which are secreted as proenzymes and require activation, comprise three subclasses, based on substrate preference: interstitial collagenases, gelatinases or type IV collagenases and stromelysins (reviewed by J. F. Woessner, 1991, see in particular Table 1).

A positive correlation between overexpression of MMPs (mostly type IV collagenases and stromelysin 3) and tumor aggressiveness has been established for several types of tumors (see I. C. Anderson et al, 1995; B. L. Lokeshwar et al, 1993; W. C. Powell et al, 1993; and J. M. Ray, 1995).

In rheumatoid arthritis and osteoarthritis, infiltrating monocytes/macrophages, inflammatory cytokine-activated synovial fibroblasts and chondrocytes produce abnormal amounts of collagenase which contributes to cartilage degradation and progression of the disease (A. M. M. Miltenburg et al, 1995).

MMPs are also involved in normal and pathological angiogenesis, as endothelial cells have to degrade the ECM to exit from the parent vessel and initiate a new capillary network (R. B. Vernon et al., 1995).

It has also been suggested that MMPs may play a role in multiple sclerosis in connection with blood-brain barrier injury (G. A. Rosenberg et al., 1996).

Taken together the above data suggest that MMPs may represent a therapeutical target in many diseases. Accordingly, various strategies based on natural or synthetic compounds are being developed to inhibit MMP activity.

ECM degradation is a tightly regulated process and collagenase proteolysis is controlled following secretion by naturally occurring inhibitors. The most significant of these are the tissue inhibitors of MMPs (TIMPs), which are locally produced by host tissues and even tumor cells (E. C. Kohn et al., 1995).

TIMPs form complexes with MMPs thereby preventing proenzyme activation and MMP catalytic activity.

Blockade of MMP production and/or activity has been shown in vitro and in vivo to prevent tumor growth and invasion (I. C. Anderson et al, 1996; X. Wang et al, 1994; A. Albini et al, 1995; A. Melchiori et al, 1992; A. Albini et al, 1994; R. Benelli et al, 1994), angiogenesis (R. E. Galardy et al, 1994; M. A. Moses, 1993), and cartilage/bone destruction in arthritis (J. G. Conway et al, 1995; E. M. O'Byrne et al, 1995; L. J. Bonassar et al, 1995).

Human chorionic gonadotropin (hCG) is a glycoprotein hormone secreted by the placenta and other normal and neoplastic tissues. It is secreted and acts so in both an endocrine and paracrine way. hCG is an heterodimer composed of noncovalently bound subunits α and β, each one having structural homology with the cystine-knot family of growth factors (platelet derived growth factor PDGF, vascular endothelial growth factor VEGF, nerve growth factor NGF and others), which are unrelated with hCG or with the family of glycoprotein hormones, as it has been recently demonstrated by the analysis of the hCG crystalline structure.

Dissociated hCG subunits can be found in urine and are often produced by tumors of the bladder, pancreas, cervix, lung, liver, and stomach as well as by trophoblastic tumors and testicular germ cell tumors.

Besides dissociated subunits, a variety of other metabolic forms of hCG can be found, particularly in urine, including hCG isoforms with various degrees of glycosylation, nicked hCG and a typical hCG-β proteolytic fragment, termed β-core which is a disulfide bound two-chain polypeptide encompassing residues 6–40 and 55–92 of the hCG-β subunit.

In addition to the above mentioned isoforms, deglycosylated hCG can be obtained by different chemical and/or biotechnological ways, as described, for example, by Kalyan and Bahl (see Kalyan et al., 1983).

β-core, as deglycosylated hCG or the single isolated subunits, does not show hCG-like biological activity, but represents a major form of immunoreactive hCG and can contaminate pharmaceutical preparations of urinary hCG.

Lunardi-Iskandar et al. (Lunardi-Iskandar et al., 1995) have shown that hCG and the hCG β-subunit inhibit KS cell lines derived from Kaposi's sarcoma, and inhibit tumor production by such cell lines in nude mice. Regression of Kaposi's sarcoma has been shown in two women during pregnancy, when the level of this hormone is high.

Applicant had also previously found (see Italian Patent Application No. RM96A309) that KS cells membranes above defined contain binding sites of β-core and deglycosylated hCG and it has been concluded that β-core itself and/or deglycosylated hCG is the agent responsible for the in vivo and in vitro biological activities found by Lunardi-Iskandar.

DESCRIPTION OF THE INVENTION

Object of the present invention is the use of hCG, hCG β-subunit, as well as active fragments and derivatives thereof, or hCG β-core in the preparation of a medicament for the prophylaxis and/or the treatment of pathologies requiring inhibition of the MMP enzymatic activity. Examples of such pathologies include: tumors, chronic inflammatory diseases, such as rheumatoid arthritis, osteoarthritis, periodontitis, multiple sclerosis and other angiogenesis-related pathologies.

Another object of the present invention are pharmaceutical compositions comprising hCG, hCG β-subunit, as well as fragments and active derivatives thereof, or hCG β-core in the presence of one or more pharmaceutically acceptable excipients, for the prophylaxis and/or treatment of pathologies requiring inhibition of the MMP enzymatic activity.

A further object of the present invention are methods for the prophylaxis and/or the treatment of pathologies requiring inhibition of the collagenase enzymatic activity comprising administering an effective amount of hCG, hCG β-subunit, as well as fragments and active derivatives thereof, or hCG β-core together with a pharmaceutically acceptable excipient.

For human therapy, the preferred dose of active ingredient is comprised between 10,000 and 500,000 Units.

The administration route of this active ingredient can be intravenous, intramuscular and subcutaneous. Other administration routes, which can guarantee the desired blood levels of active ingredient, are equally comprised in the present invention.

HCG is, preferably, recombinant and can be prepared, for example, by expression from CHO (Chinese Hamster Ovary) cells, that have been suitably transfected with the corresponding DNA, according to the technique described in EP Patent 160,699.

Suitable lyophilized pharmaceutical compositions containing hCG are described in the published PCT Patent Application WO 93/11788 and can be advantageously used according to the present invention.

Liquid pharmaceutical formulations, ready to be used, are described in the PCT Patent Application No. 95/EP/1778 and can also be advantageously used according to the present invention.

The present invention will now be described by means of the following Examples which should not be construed in any case as limiting the invention. The Example will refer to the Figures, as specified.

DESCRIPTION OF THE FIGURES

Lane 1: molecular weight markers; lane 2: not pre-treated sample; lane 3: sample pre-treated with u-hCG (40 μg/ml).

Lane 1: molecular weight markers; lane 2: thrombin (25 U); type I collagenase (5 μg).

Lane a: supernatant of KS-IST XX cells (5 μg total protein)

Lane b: supernatant of KS-IST XXVI cells (5 μg)

Lane c: supernatant of sinovial sarcoma cells (5 μg)

Lane d: supernatant of KS IMM cells (10 μg)

Lane e: supernatant of MRC5 cells (10 μg).

Lane mw: molecular weight markers.

Arrows on the left indicate the electrophoretic mobility of gelatinase A (A) and gelatinase B (B).

EXAMPLES

Example 1 r-hCG, hCG β-subunit and β-core fragment inhibit in vitro type IV collagenase produced by Kaposi's sarcoma cells.

KS-IMM is an immortalized cell line derived from an HIV-negative human Kaposi's sarcoma.

KS-IMM cells were grown at 80% confluency in DMEM supplemented with 10% FCS and then incubated for 24 hr in FCS-free DMEM. At the end of incubation the conditioned medium was collected, centrifuged for 5 min. at 1,000 rpm, diluted 1:5 with 99% ethanol and stored at −20° C. for at least 2 hr.

Ethanol precipitated proteins were collected by centrifugation at 10,000 rpm for 20 min. at 4° C. and dried.

The precipitated proteins were dissolved in 0.1 volume of 40 mM Tris-HCl, pH 7.5. Total protein concentration was determined by the method of Bradford, with a commercial kit (Bio-Rad), using as a standard BSA.

To test the collagenase activity secreted by KS-IMM cells in the conditioned medium, the precipitated proteins were submitted to zymography.

Four samples of proteins, 10 µg each, were loaded under non-reducing and non-denaturing conditions onto a 7% SDS-PAGE gel containing 0.1% gelatin (Stetler-Stevenson et al, 1989). At the end of the electrophoretic run the gel was washed for 1 hr with 2.5% Triton X-100 to remove SDS, cut into 4 pieces containing one sample each and incubated for 18 hr at 37° C. in 40 mM Tris-HCl, 0.2 M NaCl, 10 mM $CaCl_2$, pH 7.4 (collagenase buffer), in the absence and in the presence of 20 µg/ml r-hCG or 10 µg/ml hCG-β subunit or 5 µg/ml β-core fragment, respectively.

The gel pieces were then stained with a solution: 10% acetic acid, 50% methanol and 12.5% of a solution 1% Commassie Brilliant Blue (CBB) for 1 hour, and destained with 7.5% acetic acid, 25% methanol.

The collagenase activity was evidenced by a white band over a blue background. Results are shown in FIG. 1.

Example 2
r-hCG inhibits in vitro type I collagenase

Figure 1A:
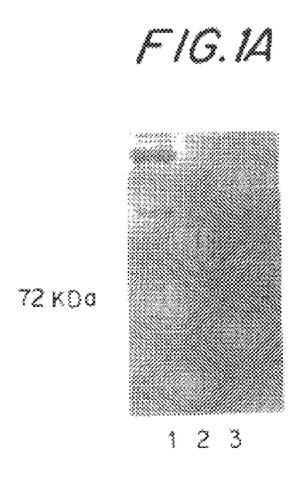
FIG. 1: shows a zymogram of proteins secreted by Kaposi's sarcoma cells KS-IMM incubated in collagenase buffer without (A) or with r-hCG 20 μg/ml (B), hCG-β subunit 10 μg/ml (C) or β-core fragment 5 μg/ml (D). KS-IMM cells secrete the 72 kD active form of MMP-2, as evidenced by a white band of lysis at the relevant MW (A). The MMP-2 band disappeared when the gels were incubated with r-hCG (B), hCG-β subunit (C) or β-core fragment (D).
Figure 1B:
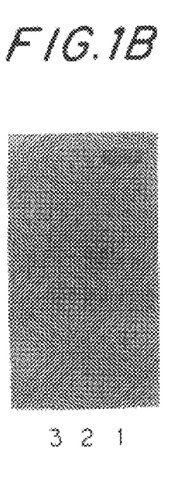
Figure 1C:
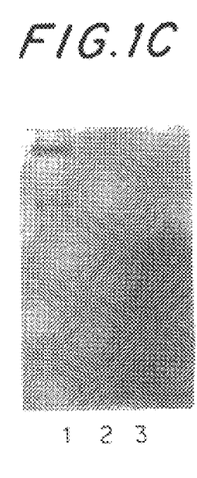
Figure 1D:
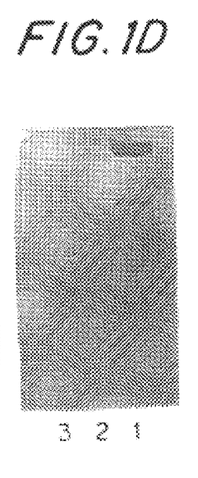
Figure 2A:
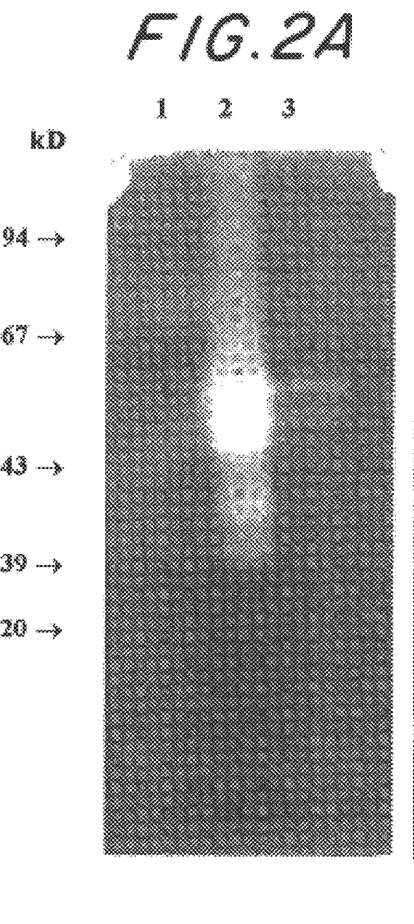
FIG. 2: shows the results of a zymogram of type I collagenase from *Clostridium histolyticum* incubated in collagenase buffer alone (a) or with the addition of r-hCG (B). The lytic band in the presence of r-hCG were much less pronounced than in collagenase buffer alone.
Figure 2B:
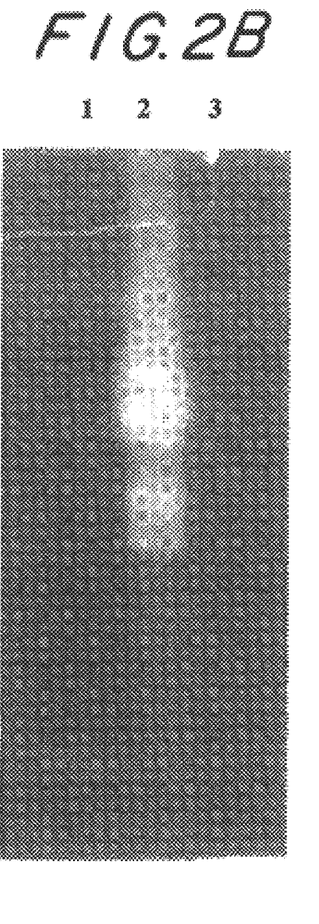

Two samples of type I collagenase from *Clostridium histolyticum* (Sigma code C 0130), 5 µg each, were submitted to zymography, as described in Example 1. At the end of the electrophoretic run the gel was cut into two pieces, incubated without and with 20 µg/ml r-hCG, and processed as in Example 1. Results are shown in FIG. 2.

Example 3
r-hCG, its β-subunit and β-core fragment in vivo inhibit the angiogenic process.
Materials and methods
Animals C57BL/6 mice and 37 (CD-1)BR nude mice were obtained from Charles River (Calco, Como, Italy).
Reagents Matrigel, an extract of the murine Engelbreth-Holm-Swarm (EHS) tumor grown in C57BL/6 mice, was produced as described previously (Kleinman et al., 1986).

Briefly, EHS tumor material was homogenized with a polytron homogenizer in a high-salt buffer (3.4 M NaCl, 50 mM Tris pH 7.4, 4 mM EDTA with 2 mM N-ethylmaleimide).

The homogenate was separated from the supernatant by centrifugation and the procedure was repeated three times. The remaining pellet was solubilized in 2 mol/l urea (2 M urea, 50 mM Tris pH 7.4, 150 mM NaCl) overnight.

The supernatant was cleared by centrifugation and dialyzed extensively against Tris-saline and finally against Dulbecco's Modified Eagles Medium (DMEM). The resulting material, Matrigel, is rich in basement membrane components (laminin, collagen IV, nidogen and perlecan) with limited quantities of growth factors (Siegal et al, 1993). The heparin used was Clarisco (Shwarz Pharma S.p.A., San Grato-Lodi, Italy).
Cell supernatants KS spindle cell cultures were used for preparation of supernatants. KS cells were grown in RPMI-1640, 10% fetal calf serum supplemented with glutamine (300 µg/ml), heparin (60 mg/500 ml) and ECGS (30 mg/500 ml).

In vivo angiogenesis

Matrigel (MG,12 mg/ml), a reconstituted basement membrane, is liquid at 4° C. and when inoculated subcutaneously solidifies into a solid gel under the skin of the mice.

Addition of heparin 2500 U/ml and 12 µl of KS supernatants (20 µl/ml) to a final volume of 600 µl results in a strong angiogenic response with neovessel formation in the Matrigel, no reaction is induced by Matrigel alone.

We tested the effects of hCG and derivatives by direct addition to the Matrigel mixture prior to injection. Four days after injection the animals were sacrificed and the gels recovered and weighed.

Haemoglobin content was measured as a direct indicator of angiogenesis. The recovered gels were minced and dispersed in water, and haemoglobin released was measured using a Drabkin reagent kit 525 (Sigma), the concentration was calculated from a standard curve and normalized to 100 mg of recovered gel.
Experimental growth of KS cells in vivo Four distinct experiments were carried out, under different conditions:
1) KS IMM cell cultures were pretreated in vitro with β-core 0.5 µg/ml for 96 hours before injection into nude mice.

Two groups of animals were used; the control group (8 mice) was injected i.p. with physiological solution, the second (9 mice) with 1 µg/30 gr mouse β-core 96 hours before cell inoculation.

The dosage of β-core in the first experiment was calculated on the basis of human administration, using equivalent doses taking into account the relation between human and murine body weight and stoichiometric proportion between hCG and the β-core.

All the mice were injected with $5\times10^6$ KS IMM cells suspended in 250 µl of MG.

The treatments were continued daily up to the end of the experiment.
2) KS IMM were pretreated in vitro with 1.6 µg/ml of r-hCG or 1 µg/ml of β-subunit 24 hours before inoculation into nude mice.

Animals (8 for each group) were also pretreated with physiological solution or with r-hCG 12.5 µg/30 gr mouse or β-subunit 7.8 µg/30 gr mouse 24 hours before inoculation.

Animals were then inoculated s.c. with $5\times10^6$ KS IMM cells without MG. For intralesional treatment r-hCG 12.5 µg/30 gr mouse every 48 hours or β-subunit 7.8 µg/30 gr mouse daily for 3 weeks were used.

Controls were treated daily by intralesional injection of physiological solution. Doses were chosen on the basis of the paper of Lunardi-Iskandar et al. (Lunardi-Iskandar et al., 1995), in which 12.5 µg/30 gr mouse of u-hCG were utilized.

We have utilized the same dose for r-hCG and the corresponding stoichiometric dosage (7.8 µg/30 gr mouse) for the β-subunit.
3) Cells and nude mice were not pretreated. Animals (8 for each group) were inoculated s.c. with $5\times10^6$ KS IMM cells per 0.2 ml of serum-free medium plus MG (250 µl, 10 mg/ml).

Animals were treated i.p. with r-hCG 16 µg/30 gr mouse or β-core 5 µg/30 gr mouse 3 times the first week and daily for the subsequent weeks. This experiment required 21 days.
4) This experiment was conducted as in 3, but was stopped at the initial phase of tumor growth (13th day).

We have utilized 7 mice for the control group, 6 for the β-subunit 10 µg/mouse treated group and 7 for the β-core 5 βg/mouse treated group.

One of the mice treated with β-core died at the 8th day after inoculation and is not included in our results; this mouse however showed a hardly palpable tumor.

At the 13th day, tumors were excised, weighed and processed for angiogenesis evaluation, measured as haemoglobin content.

Gelatin zymography

Gelatin zymographs, used to visualize the type-IV collagenases which also have a characteristic gelatinase activity (gelatinase A and B) were performed according to Heussen and Dowdle (Heussen and Dowdle, 1980) with minor modifications.

SDS-PAGE gel (7%) containing co-polymerized gelatin at a final concentration of 0.6 mg/ml or 0.06% w/v were prepared. Samples of proteins (10 μg for KS IMM and MRC5 cell lines and 5 μg for KS spindle cell lines and sinovial sarcoma cell lines) were redissolved in 40 mM Tris, pH 7.5, and electrophoresed in SDS-PAGE gel (7%) containing co-polymerised gelatin (0.1%).

After electrophoresis the gel was washed 4 times (30 min each) in 2.5% Triton X100 to remove SDS, cut into small identical portions and incubated for 18 hours at 37° C. in 40 mM Tris, 200 mM NaCl, 10 mM $CaCl_2$ buffer, pH 7.4, in either the absence (−) or the presence (+) of r-hCG 16 μg/ml.

After digestion the gel was stained with a solution: 10% acetic acid, 50% methanol and 12.5% of a solution 1% Coomassie brilliant blue for 1 hour, and destained with 7.5% acetic acid and 20% methanol.

Enzyme-digested regions were identified as white bands against a blue background.

Results r-hCG and B-subunit inhibit the angiogenic response in Matrigel (MG) sponges In this experimental model, MG alone can be utilized as a negative control, while KS-supernatants in the presence of heparin represent a positive control, since they induce neovascularization into the gel.

The addition of hCG to the MG containing KS-supernatants and heparin, reduced the formation of new blood vessels. The inhibitory effect was also evaluated by measuring the haemoglobin content.

Four days after MG injection, animals were sacrificed and gels extracted for evaluation of angiogenesis.

Here we report the results of the first experiment; r-hCG 16 μg/ml and β-subunit 10 μg/ml were tested. The data are summarized in Table 1.

hCG and derivatives reduce experimental growth of KS cells in vivo in the initial phase by control of the angiogenic process Inoculation of KS IMM cells subcutaneously into nude mice promotes the formation of an experimental tumor. Four assays were conducted, using this experimental model.

The first experiment was conducted by inoculation of KS IMM cells with Matrigel.

Figure 3A:
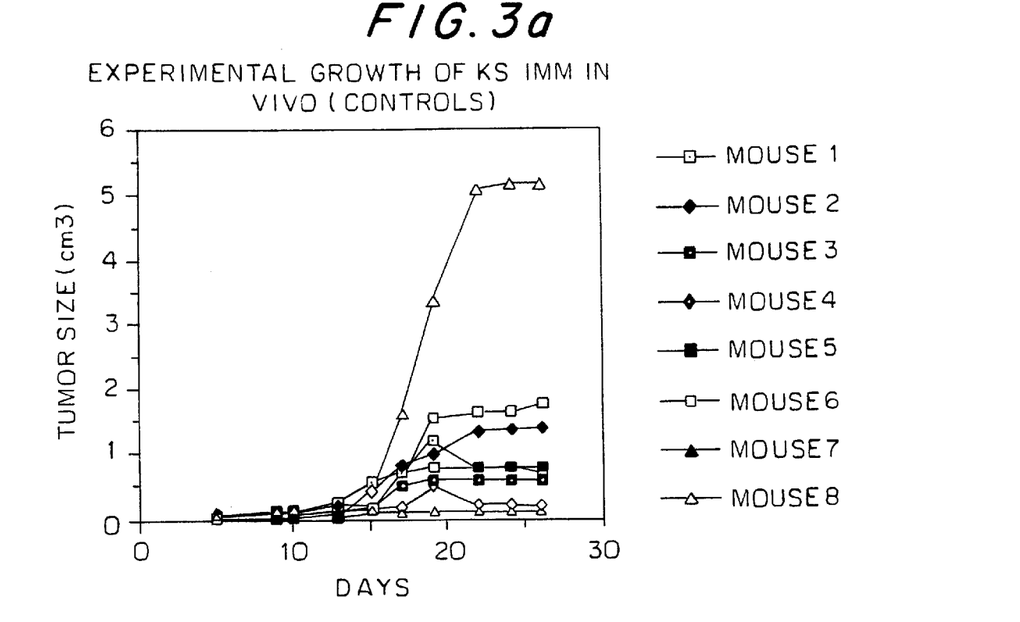
FIG. 3A: shows the experimental growth of KS IMM cells (with MG) inoculated in nude mice, as controls (1st experiment).
Figure 3B:
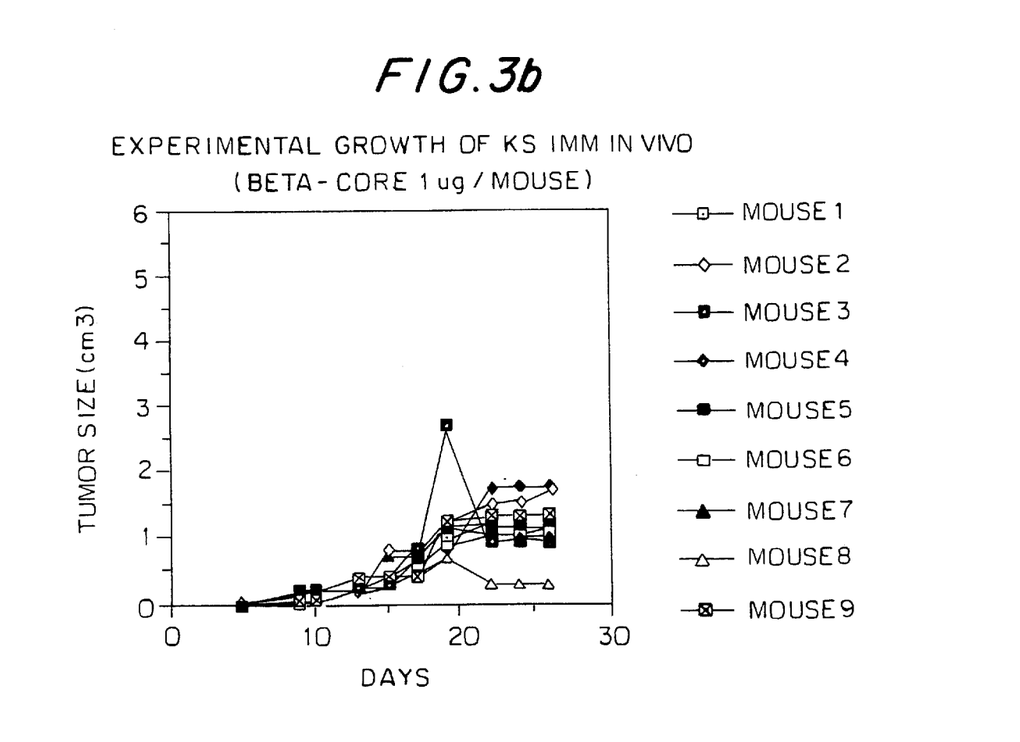
FIG. 3B: shows the experimental growth of KS IMM cells (with MG) inoculated in nude mice treated with 1 μg/mouse hCG β-core (1st experiment).

A rapid tumor growth was obtained. However the results (FIG. 3A–3B) showed no difference between the control and the β-core treated group, because possibly the β-core intraperitoneal dosage (1 μg/mouse) was too low.

Figure 4A:
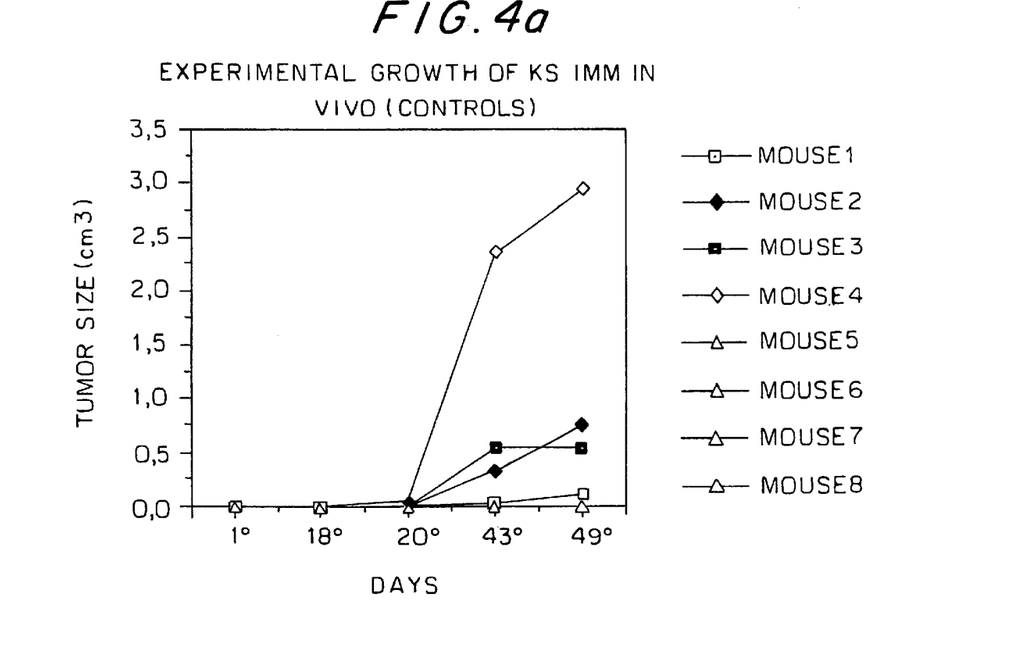
FIG. 4A: shows the experimental growth of KS IMM cells (with MG) inoculated in nude mice, as controls (2nd experiment).
Figure 4B:
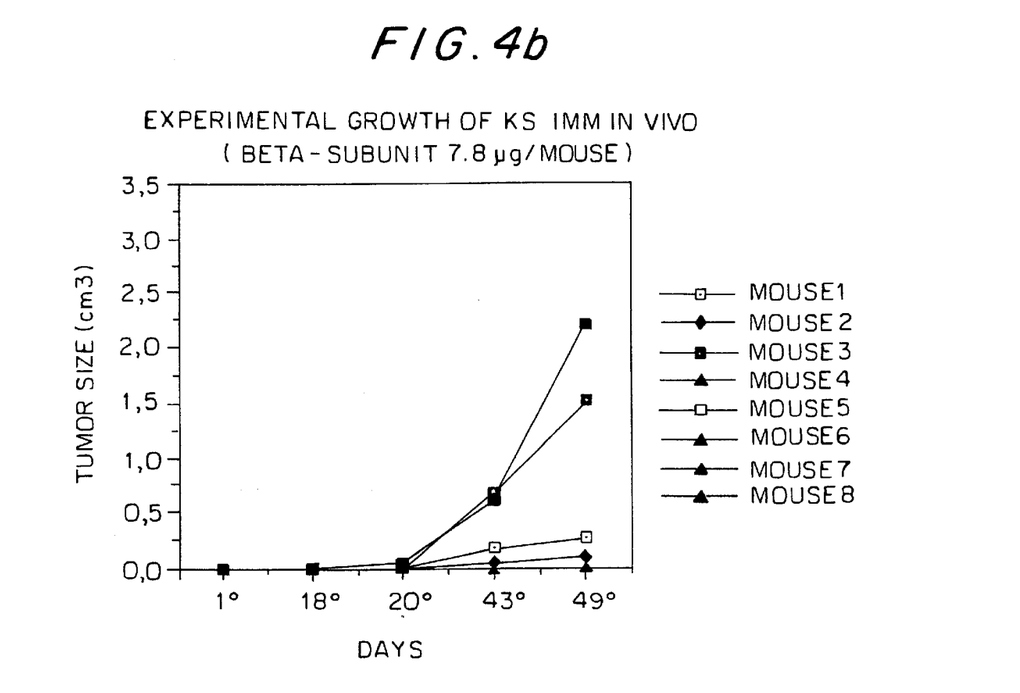
FIG. 4B: shows the experimental growth of KS IMM cells (with MG) inoculated in nude mice treated with β-subunit 7.8 μg/mouse.
Figure 4C:
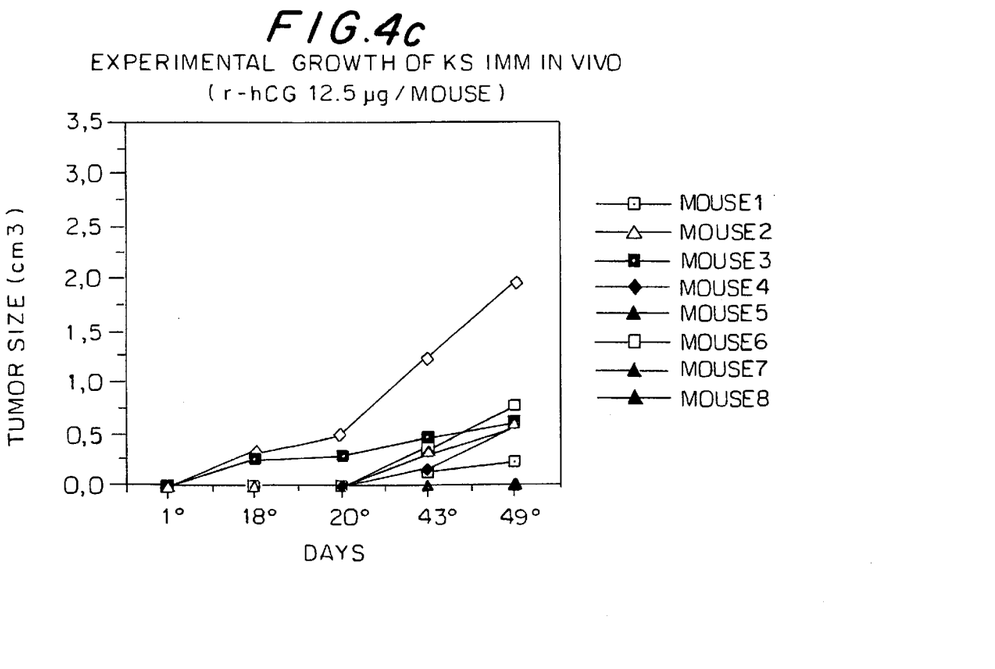
FIG. 4C: shows the experimental growth of KS IMM cells (with MG) inoculated in nude mice treated with r-hCG 12.5 μg/mouse.

In the second experiment (FIG. 4A–4B) KS IMM cells were injected without Matrigel, to test intralesional inoculation of substances. The absence of Matrigel determined a delayed and irregular tumor growth: in the control group, as well as in the β-subunit treated group, 4 mice out of 8 showed no tumor; in the r-hCG treated group, 2 mice out of 8 showed no tumor.

In the third experiment (FIG. 5A–B and FIG. 6A–6C), after that appropriate general condition had been established, r-hCG (16 μg/30 gr mouse, corresponding to 0.5 mg/kg) and β-core (5 μg/30 gr mouse) were tested: a reduction of tumor growth in the initial phase was in fact observed.

In the following experiment, with the same experimental conditions, r-hCG (16 μg/30 gr mouse) and β-core (5 μg/30 gr mouse) were tested: the analysis of tumor samples at the 13th day confirmed that hCG and derivatives are able to control the vascularization of KS lesions in vivo, reducing both tumor growth and haemoglobin content in the initial phase (Tables 2–3).

Haemoglobin measurement was conducted on tumor samples as an in vivo angiogenesis assay.

hCG and derivatives inhibit partially the gelatinolytic activity of MMP2

Supernatants from 5 cell lines (KS IMM cell line, KS IST XX spindle cell line derived from a HIV+ patient, KS IST XXVI spindle cell line derived from a HIV− patient, a sinovial sarcoma cell line and MRC5 human fibroblast cell line) were analyzed on gelatin zymography, in the absence or the presence of the collagenase buffer of hCG and derivatives.

R-hCG (20 μg/ml), β-subunit (10 μg/ml) and the β-core fragment (5 μg/m l) added in the collagenase buffer totally inhibit the gelatinolytic activity of 72 kDa type-IV collagenase (MMP2) of KS IMM (FIG. 1); lower dosages (r-hCG 1.6 μg/ml, β-subunit 1 μg/ml and β-core 0.5 μg/ml) yield a partial inhibition.

Figure 7A:
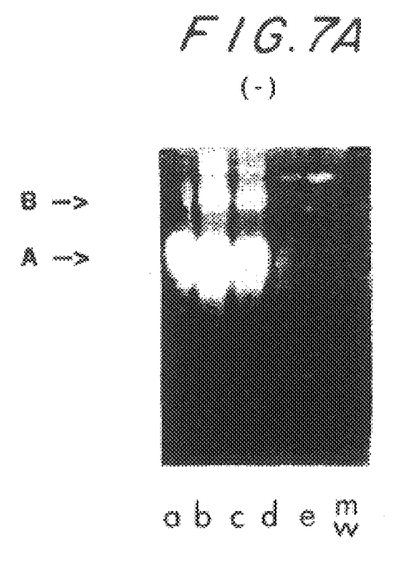
FIG. 7: shows the results of zymographic analyses of 5 cell lines, in either the absence (−) or the presence (+) of r-hCG, added to the collagenase digestion buffer at the concentration of 16 μg/ml.
Figure 7B:
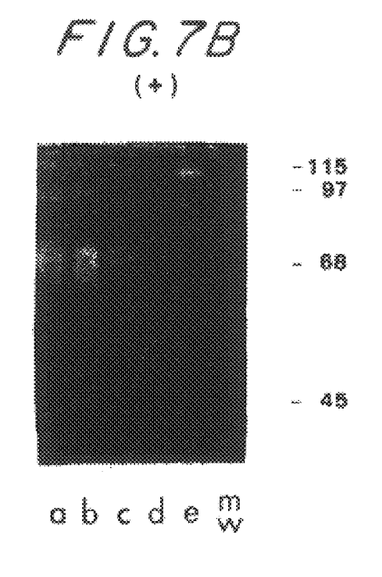

For the other tested cell lines which produced higher quantities of gelatinase A (KS spindle cell lines and the sinovial sarcoma cell line), the inhibition by r-hCG 16 μg/ml was partial (FIG. 7). These lines required higher doses of substances.

Discussion

In order to evaluate the best procedure for the in vivo assays, four experiments of experimental growth of KS cells in nude mice were carried out, under different conditions. In the first experiment (FIG. 3A–3B), KS cells were inoculated with MG; in the second (FIG. 4A–4B), for problem-free intralesional inoculation of substances, cells were injected without MG.

Comparing the two correspondent graphics, we can see that the inoculation of KS cells with MG favors the onset of tumor growth. This condition was therefore maintained in the following experiments. After the first and the second experiment, in which pretreatment was ineffective, the pretreatment was not repeated.

Figure 5A:
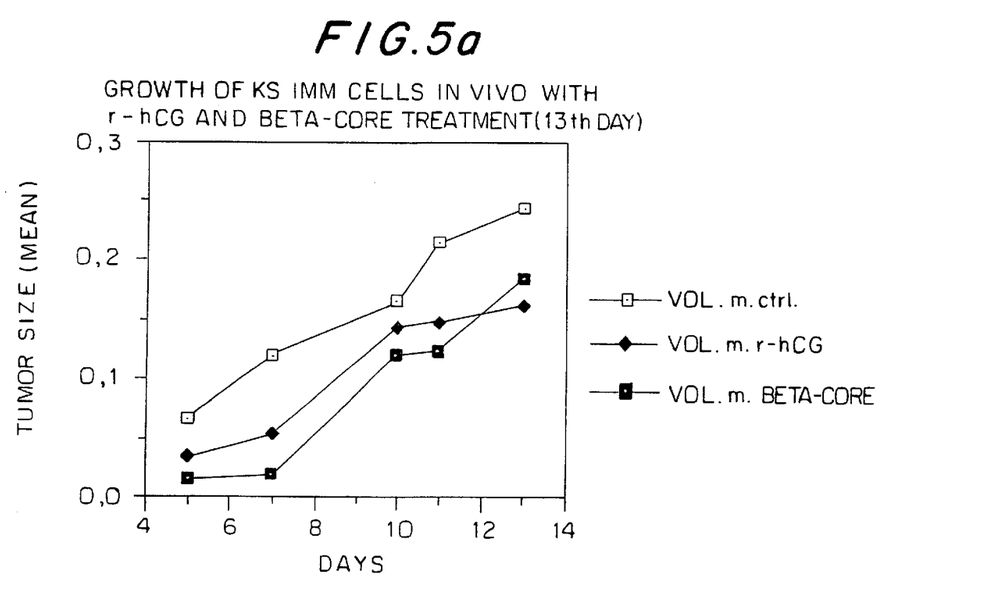
FIG. 5A: shows the experimental growth of KS IMM cells (3rd experiment) inoculated in nude mice treated with r-hCG or hCG β-core; in particular, the difference in growth up to the 13th day following inoculation is shown.
Figure 5B:
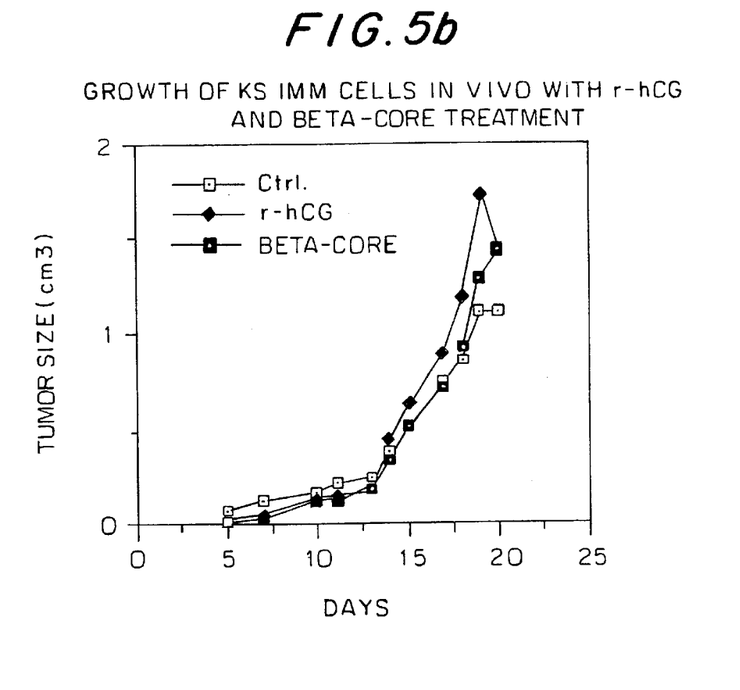
FIG. 5B: shows the experimental growth of KS IMM cells (3rd experiment) inoculated in nude mice treated with r-hCG or hCG β-core; in particular, it shows that the tumor growth progressed similarly in control and treated groups.
Figure 6A:
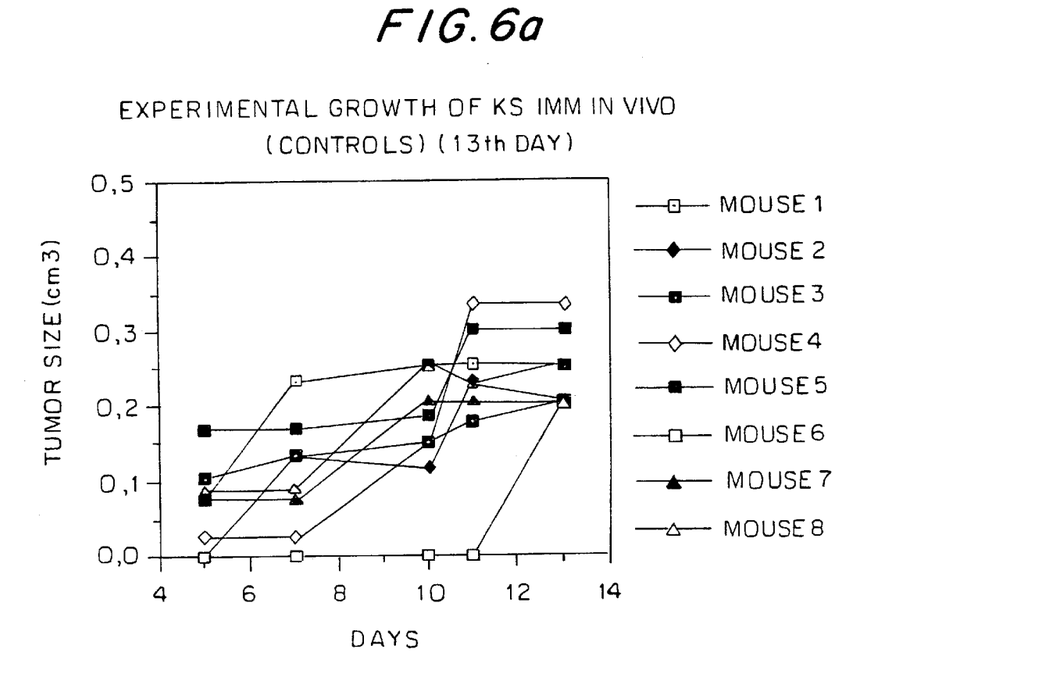
FIG. 6A: shows the experimental growth of KS IMM cells inoculated in nude mice in controls, indicating the progression of the tumor at the 13th day.
Figure 6B:
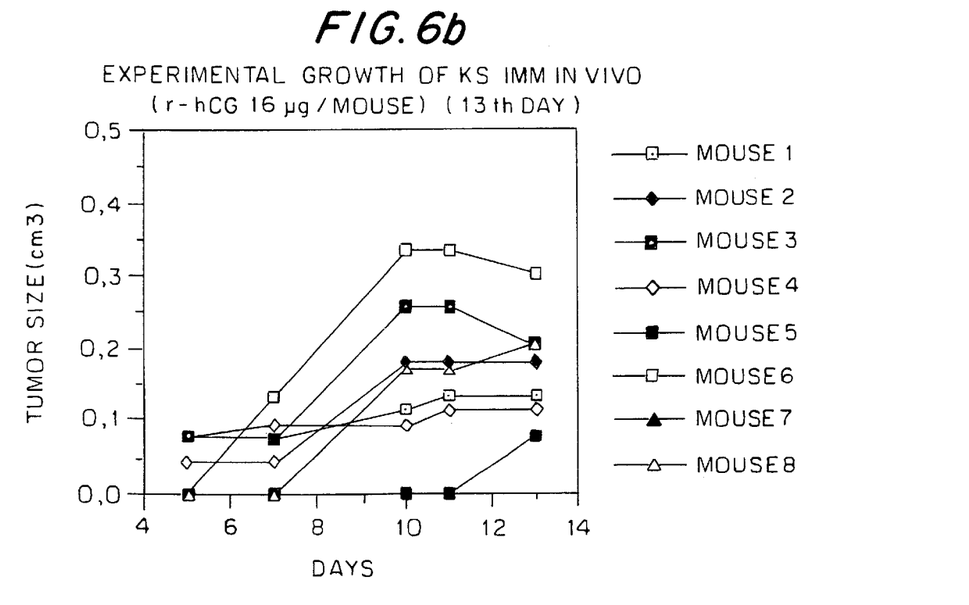
FIG. 6B: shows the experimental growth of KS IMM cells inoculated in nude mice treated with r-hCG 16 μg/mouse, indicating the progression of the tumor at the 13th day.
Figure 6C:
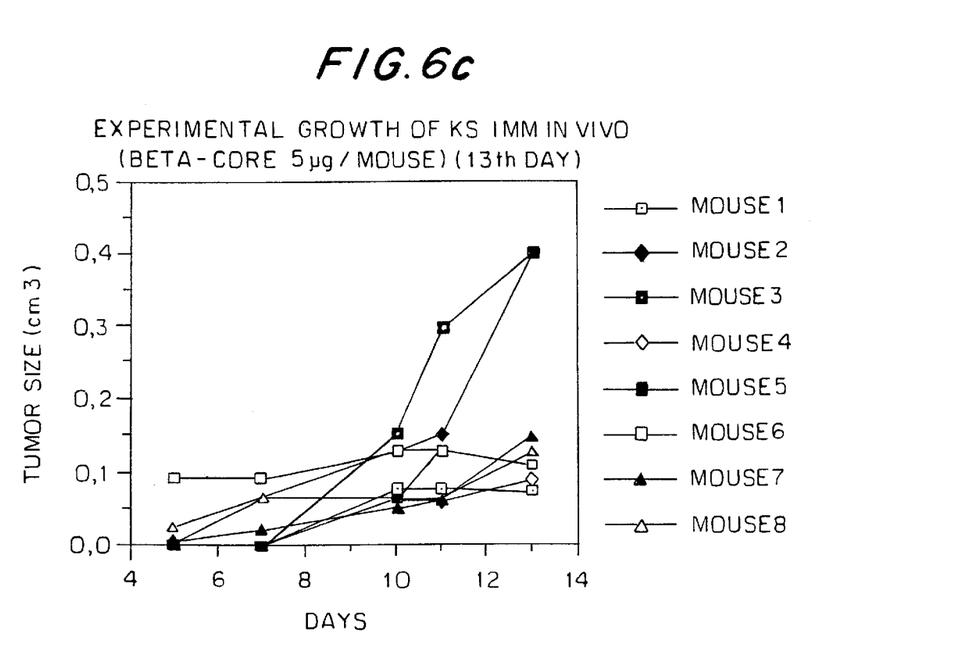
FIG. 6C: shows the experimental growth of KS IMM cells inoculated in nude mice treated with hCG β-core 5 μg/mouse, indicating the progression of the tumor at the 13th day.

In the 3rd experiment, a reduction in growth, up to the 13th day following the inoculation (FIG. 5A and 6A–6C) can be observed. The difference in size between control and treated groups was significant, with a reduction to 69% for r-hCG and 57% for β-core at the 11th day, and to 66% for r-hCG and 75% for β-core at the 13th day. Subsequently, all groups progressed similarly (FIG. 5B).

A similar behavior has been observed with a different antiangiogenic substance, thrombospondin-1, see (P. Boukamp, 1996).

To confirm the antiangiogenic activity of hCG and derivatives, the fourth experiment (see results in Tables 1–3) has been carried out in the same manner, but sacrificing the mice when the tumor growth was in the initial phase.

The number of samples in the Tables indicate the pieces of tumor taken for measurement, one for each animal. The analysis of tumor weight and haemoglobin content in the tumor samples showed that the inhibition of tumor growth was in fact associated with reduced angiogenesis.

The results of the gelatin zymography confirm that high doses of substances are necessary for the inhibition of metalloprotease activity. No inhibition of collagenase activity produced by KS IMM cells can be observed with the dosages which can inhibit in vitro growth (1.6 μg/ml r-hCG, 0.5 μg/ml β-core), but a total inhibition can be achieved with a higher dosage (20 μg/ml r-hCG, 10 μg/ml of β-subunit and 5 μg/ml of β-core). For the KS spindle cell lines and the synovial sarcoma line (which express a higher quantity of MMP2) the inhibition is in fact partial, given the higher enzymatic activity.

TABLE 1

Inhibition Of Angiogenesis Induced In Matrigel By KS-26 Products, Measured As Absorbance At 540 nm

| Treatment | Mean | Range (OD At 540 Nm) | Number Of Samples | % |
|---|---|---|---|---|
| control | 0.280 | 0.070–0.706 | 6 | 100 |
| r-hCG 16 μG/ml | 0.015 | 0.000–0.040 | 6 | 5 |
| β-subunit 10 μg/ml | 0.013 | 0.006–0.020 | 6 | 5 |

TABLE 2

Inhibition Of KS IMM Angiogenesis Measured As Haemoglobin Content

| Treatment | Haemoglobin gr/dl Mean | Range | Number Of Samples | % |
|---|---|---|---|---|
| control | 0.280 | 0.25–1.77 | 7 | 100 |
| β-subunit 10 μG/mouse | 0.620 | 0.22–1.32 | 6 | 85 |
| β-core 5 μg/mouse | 0.450 | 0.01–1.11 | 6 | 64 |

TABLE 3

Inhibition Of KS IMM Tumor Growth Measured As Tumor Weight

| Treatments | Haemoglobin gr/dl Mean | Range | Number Of Samples | % |
|---|---|---|---|---|
| control | 0.444 | 0.17–0.71 | 7 | 100 |
| β-subunit 10 μG/mouse | 0.403 | 0.23–0.54 | 6 | 91 |
| β-core 5 μg/mouse | 0.305 | 0.21–0.41 | 6 | 69 |

References

1. Albini et al, *AIDS* 8, 1237–1244, 1994;
2. Albini et al.: *Int. J. Cancer,* 61, 121–129, 1995;
3. Albini et al: AIDS, in press
4. Anderson et al, *Cancer Res.* 55, 4120–4126, 1995;
5. Anderson et al, *Cancer Res.* 56, 715–718, 1996;
6. Benelli et al, *Oncol. Res.* 6, 251–257, 1994;
7. Bonassar et al, *Arthritis Rheum.* 38, 1678–1686, 1995;
8. Boukamp, The 9th International Conference of the International Society of Differentiation (ISD), *S*38, *Program and Abstract Book,* Pisa (IT) Sep. 28–Oct. 2, 1996;
9. Conway et al, *J. Exp. Med.* 182, 449–457, 1995;
10. Dodwell et al., *Cancer Treat. Rev.* 19, 283–296, 1993;
11. Galardy et al, *Cancer Res.* 54, 4715–4718, 1994;
12. Gill et al: *N. Engl. J. Med.* 335, 1261-9, 1996;
13. Heussen and Dowdle: *Anal. Biochem.,* 102, 196–202, 1980;
14. Kalyan et al., *J. Biol. Chem.* 258, 67–74, 1983;
15. Kleinman et al: *Biochemistry,* 25, 312–318, 1986;
16. Kohn et al., *Cancer Res.* 55, 1856–1862, 1995;
17. Lokeshwar et al, *Cancer Res.* 53, 4493–4498, 1993;
18. Lunardi-Iskandar et al.: *Nature,* 375, 64–68, May 4, 1995;
19. Melchiori et al, *Cancer Res.* 52, 2353–2356, 1992;
20. Miltenburg et al, *J. Immunol.* 154, 2655–2667, 1995);
21. Moses et al., *Clin. Exper. Rheumatol.* 11 (Suppl. 8), S67–S69, 1993);
22. O'Byrne et al, *Inflamm. Res.* 44 Suppl. 2, S117–118, 1995;
23. Powell et al, *Cancer Res.* 53, 417–422, 1993;
24. Ray et al., *EMBO J.* 14, 908–917, 1995;
25. Rosenberg et al., *Neurology,* 46(6), 1626–1632, 1996;
26. Siegal et al: *Cancer Lett.,* 69, 123–132, 1993;
27. Stetler-Stevenson et al, *J. Biol. Chem.* 264, 1353–1356, 1989;
28. Vernon et al., *Am. J. Pathol.* 147, 873–883, 1995
29. Wang et al, *Cancer Res.* 54, 4726–4728, 1994;
30. Woessner, *FASEB J.,* 5, 2145–2154, 1991.

What is claimed is:

1. A method for treatment of a pathology requiring inhibition of matrix metalloprotease enzymatic activity selected from the group consisting of chronic inflammatory diseases, multiple schlerosis, and angiogenesis-dependent diseases with the proviso that the pathology is not a tumor or cancer, comprising administering to a subject in need thereof one or more pharmaceutically acceptable excipients and an effective amount of recombinant heterodimeric human chorionic gonadotropin (rhCG).

2. The method of claim 1, wherein the pathology is a chronic inflammatory disease.

3. The method of claim 1, wherein the pathology is multiple sclerosis.

4. The method of claim 1, wherein the pathology is an angiogenesis-dependent disease that is not a tumor or a cancer.

* * * * *